US00PP29396P2

(12) United States Plant Patent
Hansen

(10) Patent No.: US PP29,396 P2
(45) Date of Patent: Jun. 12, 2018

(54) ***HEUCHERA* PLANT NAMED 'APPLETINI'**

(50) Latin Name: ***Heuchera* hybrid**
Varietal Denomination: Appletini

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days. days.

(21) Appl. No.: 15/530,030

(22) Filed: Nov. 21, 2016

(51) Int. Cl.
*A01H 5/12* (2018.01)
*A01H 5/02* (2018.01)

(52) U.S. Cl.
USPC ..... Plt./440
CPC ..... *A01H 5/02* (2013.01); *A01H 5/12* (2013.01)

(58) Field of Classification Search
USPC ..... Plt./440
CPC ... A01H 5/02; A01H 5/00; A01H 5/12; A01H 5/025
See application file for complete search history.

(56) References Cited

PUBLICATIONS

Michell's 2015-16 Availability List Walters Gardens, Inc. retrieved on Nov. 13, 2017, retrieved from the Internet at http://www.michells.com/availabilities/Waltersavailability.pdf, pp. 1, 15 and 28 (Year: 2016).*

* cited by examiner

*Primary Examiner* — June Hwu

(57) ABSTRACT

The new and distinct hybrid of *Heuchera* plant named 'Appletini' with cordate foliage of lime green to light chartreuse with a thick silver overlay between the veins on top surface and slight rosy blush underneath in the fall and strong yellowish pink in the spring. Large flowers are deep rich red on compact panicles with some reblooming in the fall. The new plant is vigorous, compact in leaf and flower habit and suitable for use in the landscape en masse, an accent or in containers or cut flowers.

1 Drawing Sheet

Botanical denomination: *Heuchera* hybrid.
Variety denomination: 'Appletini'.

BACKGROUND OF THE INVENTION

The present invention relates to a new and distinct cultivar of Coral Bells in the Saxifragaceae family and given the cultivar name of 'Appletini'. *Heuchera* 'Appletini' was hybridized by the inventor on Jan. 30, 2012 at a nursery in Zeeland, Mich., USA and initially assigned the breeder code 12-113-8. The seed or female parent was unreleased proprietary hybrid 11-8-1 (not patented) and the pollen or male parent was an unreleased proprietary hybrid known only by the breeder code K11-52-16 (not patented) and the parents of K11-52-16 are 'Mocha Mint' (not patented) and 'Milan' (U.S. Plant Pat. No. 21,682). The new invention has a mixture comprising *Heuchera americana, H. brizoides, H. micrantha* and *H. villosa* in the pedigree.

*Heuchera* 'Appletini' was first selected in the spring of 2013 and passed final evaluation in 2014 from among thousands of other seedlings from the same cross and hundreds of other crosses. *Heuchera* 'Appletini' has been asexually propagated by division at the same nursery in Zeeland, Mich. in 2014 and by careful shoot tip tissue culture propagation, and the resultant plants have remained stable and continued to exhibit the same characteristics as the original plant for multiple generations.

No plants of *Heuchera* 'Appletini' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

The female parent has 'Ruby Bells' (not patented) and 'Miracle' U.S. Plant Pat. No. 20,274. In comparison to the parents and predecessors, *Heuchera* 'Appletini' has more chartreuse foliage with silvery marbling between the veins and rounded lobes and deeper reddish flowers. Further comparison of the parents is not possible as neither plants nor photographs were maintained. Other similar coral bells include: 'Sweet Tart' U.S. Plant Pat. No. 24,573 which has smaller leaf blades and smaller habit with lighter colored flowers and panicles with less pronounced branching; 'Ruby Bells' (not patented) has foliage that is more green than the new plant and flowers that are smaller; compared to 'Havana' U.S. Plant Pat. No. 22,087 the new plant has more rounded leaf blade lobes and darker reddish flowers.

*Heuchera* 'Appletini' differs from its parents as well as all other coral bells known to the applicant in the following combined traits:

1. The foliage color is lime green to light chartreuse with a thick silver overlay above and slight rosy blush underneath.
2. Overall leaf shape is cordate with rounded lobes.
3. Early-summer the new plant produces dense scapes of rich ruby red flowers.

4. The new plant occasionally reblooms in the fall when deadheaded.
5. The new plant is vigorous and compact in leaf and flower habit.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
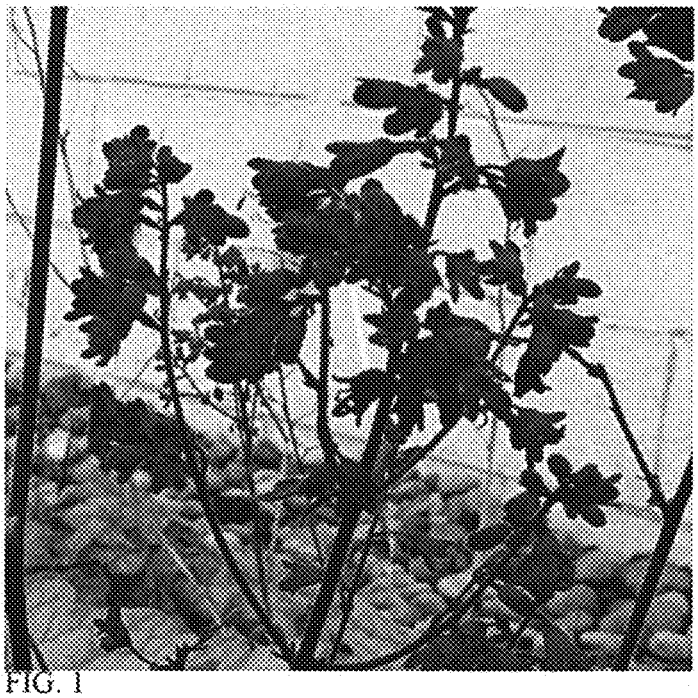
FIG. 1 shows a close-up of the panicle with flowers and buds.
Figure 2:
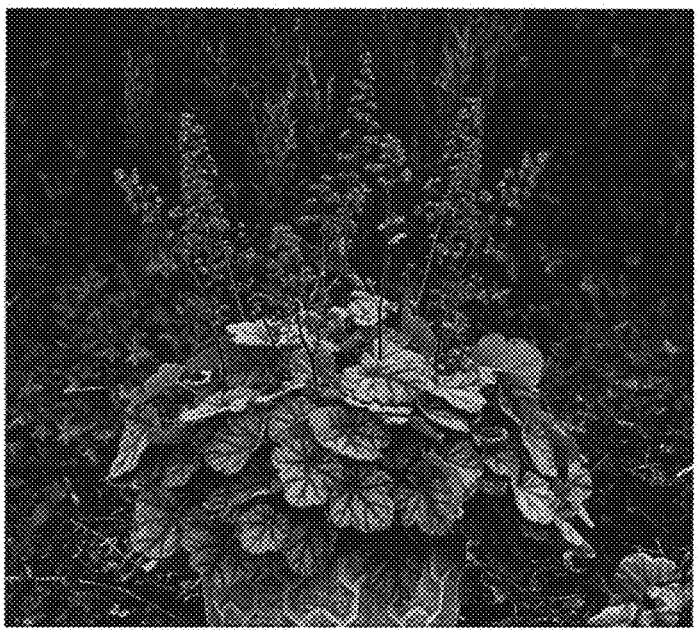
FIG. 2 shows a two-year-old plant in a container in full flower in early summer.

The following description is based on a two-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female or seed parent was unreleased proprietary hybrid 11-84 and the pollen or male parent was a proprietary unreleased hybrid known only by the breeder code K11-52-16;

Plant habit: Hardy herbaceous perennial with basal rosette of foliage; mounded foliage about 22.0 cm tall and 52.0 cm in diameter with scapes to about 50 cm long; stems to about 5.0 cm long and 1.5 cm diameter at base with about 20 to 25 leaves per stem and ten main stems per plant;

Roots: Fibrous, finely branched;

Growth rate: Rapid, rooting from cutting in two weeks and finishing in three-liter container in about 3 months;

Foliage: Cordate, minutely puberulent adaxial and abaxial; palmately shallowly lobed with five main lobes dissected less than one-third the way to petiole; apex rounded, base cordate to auriculate with basal lobes imbricate to about 0.5 cm; margins crenate to mucronate, hirsutulous; slightly indented adaxial veins; lustrous abaxial, matte adaxial; held nearly horizontal; margin undulation weak to absent;

Leaf blade size: To about 10.5 cm wide and 10.5 cm long, average about 9.5 cm wide and 9.5 cm long;

Leaf color: Spring and young emerging leaves adaxial nearest RHS 145A with region near veins nearest RHS 144B and with no silver marbling between the veins, spring young emerging leaves adaxial nearest RHS 145B with undertone of nearest RHS 37A; adaxial mature mid-season leaves nearest RHS 160A in region between the veins and region closely surrounding the veins nearest RHS 144A; mature mid-season leaves abaxial between RHS 160A and RHS N144A; late fall leaves adaxial region between the veins between RHS 191B and RHS 191C and region closely surrounding the veins nearest RHS 137B; late fall abaxial surface nearest RHS 147C with blush of nearest RHS 186B; mid-winter leaves adaxial region variable, some regions comprising nearest RHS 158A, others nearest RHS 138A, RHS 138B and others a blend between RHS N170C and RHS N170B; mid-winter abaxial color variable comprising nearest RHS 158A, RHS 180D and others RHS 138B;

Leaf quantity: Dense, about 200 per plant;

Veins: Palmate, hirsutulous abaxial and adaxial; costate abaxial, slightly impressed adaxial;

Vein color: Emerging or early spring foliage abaxial nearest RHS 145D; emerging or early spring foliage adaxial nearest RHS 145C in proximal one-third with distal one-third becoming nearest RHS 145A; mid-season adaxial blend between RHS 151D and lighter than RHS 153D, mid-season abaxial nearest RHS N145C; late fall abaxial between RHS 145B and RHS 145C; adaxial between RHS 151A and RHS 151C in proximal one-third and distal one-third becoming nearest RHS 137B;

Petiole: Terete, amplexicaul; with pubescent hairs to about 1.0 mm long; average about 15.0 cm long and about 4.0 mm diameter in center and 13.0 mm at base including stipule;

Petiole color: Emerging leaf blend between RHS 145A and RHS 145B; mature leaf nearest RHS 145A with undertones of nearest RHS 186C; late fall petioles nearest RHS 144A with occasional light blush of nearest RHS 182D;

Stipule: At base of petiole, about 1.3 cm long and about 1.3 cm wide at base;

Stipule color: Adaxial and abaxial nearest RHS 145C;

Peduncle: Panicle; terete; stiff; pubescent; upright; to about 50.0 cm long and 4.5 mm diameter at base, average about 46.0 cm tall and 4.0 mm diameter; about twelve per plant with up to 150 flowers per panicle, average about 125; heavily-branched panicle with up to 10 branches up to 16.0 cm long and 2.0 mm diameter decreasing distally, average 8 branches per panicle; lower branches upward becoming outward distally; flower density moderate;

Flowering longevity: Panicle effective for about three to four weeks with some repeat in the fall if deadheaded;

Peduncle color: Nearest RHS 183A in upper portion when mature, nearest RHS 146C with blush of nearest RHS 183A in lower portion;

Pedicel: Terete, finely puberulent, average about 4.0 mm long and 0.5 mm diameter;

Pedicel color: Nearest RHS N186C;

Buds one day prior to opening: Oblong ellipsoid; rounded apex and rounded base; puberulent to glandular; about 6.0 mm long and 3.5 mm diameter;

Bud color one day prior to opening: Nearest RHS 46A;

Flower: Perfect, campanulate, actinomorphic, about 9.0 mm long and 8.0 mm in diameter at face; individual flowers lasting about 4 days on plant or as cut flower;

Flower attitude: Mostly outward;

Calyx: Five, apex rounded, base fused in proximal 2.0 mm to form hypanthium; pubescent to glandular abaxial, glabrous adaxial; about 3.0 mm long and 3.0 mm wide;

Calyx color: Abaxial nearest RHS 53A, adaxial nearest RHS 53A;

Petals: Five, lanceolate, rounded apex and attenuate base, entire, glabrous abaxial, puberulent adaxial, about 9.0 mm long and 1.5 mm wide in middle;

Petal color: Abaxial nearest 46A, adaxial apex nearest RHS 46A, base lightening to nearest RHS 56D;

Androecium: Five adnate to adaxial petal about 1.0 mm from base;

*Filaments*.—Five, thin, glabrous; about 4.5 mm long and less than 0.3 mm diameter; color nearest RHS N155C with blush of nearest RHS 62C distally.

*Anthers*.—Ellipsoidal, distinct, basifixed, longitudinal; about 0.5 mm long and less than 0.4 mm across; color nearest RHS 11D.

*Pollen*.—Abundant; color nearest RHS 11D.

Gynoecium: One, two-beaked; half-inferior; bifid style with pistil split at ovary; 7.5 mm long;

*Style*.—Bifid; split apart at apex of ovary; about 6.5 mm long and about 1.0 mm diameter; color nearest RHS N155C with a blush of nearest RHS 62C distally.

*Stigma*.—Acute apex, about 0.1 mm diameter; color nearest RHS N155C.

*Ovary*.—Half-inferior, about 2.5 mm long and 2.0 mm diameter; ellipsoidal to globose, base rounded; color nearest RHS 150D.

Fruit and seeds have not yet been observed;

Disease and pest tolerance: The new plant grows best with ample moisture and drainage in either sun or shade. It is more tolerant of hot and humid environments than typical coral bells. Cold hardy from USDA zones 4 to 9. Other resistance and tolerance outside of that normal for *Heuchera* is not known.

It is claimed:

1. The new and distinct coral bells plant named *Heuchera* 'Appletini' as herein described and illustrated.

* * * * *